United States Patent
Bajramovic et al.

(10) Patent No.: US 12,078,862 B2
(45) Date of Patent: Sep. 3, 2024

(54) ARRANGEMENT AND METHOD FOR COMPENSATING FOR THE TEMPERATURE DEPENDENCE OF A FACET LENS FOR DETERMINING THE TOPOGRAPHY OF AN EYE

(71) Applicant: Carl Zeiss Meditec AG, Jena (DE)

(72) Inventors: Ferid Bajramovic, Mamming (DE); Rico Fuchs, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 595 days.

(21) Appl. No.: 17/295,006

(22) PCT Filed: Nov. 20, 2019

(86) PCT No.: PCT/EP2019/081926
§ 371 (c)(1),
(2) Date: May 18, 2021

(87) PCT Pub. No.: WO2020/104525
PCT Pub. Date: May 28, 2020

(65) Prior Publication Data
US 2022/0035116 A1 Feb. 3, 2022

(30) Foreign Application Priority Data
Nov. 21, 2018 (DE) .................... 10 2018 219 902.7

(51) Int. Cl.
*A61B 3/10* (2006.01)
*A61B 3/107* (2006.01)
(Continued)

(52) U.S. Cl.
CPC .............. *G02B 7/008* (2013.01); *A61B 3/107* (2013.01); *G01B 11/255* (2013.01)

(58) Field of Classification Search
CPC ....... A61B 3/107; G01B 11/255; G02B 7/008
(Continued)

(56) References Cited

U.S. PATENT DOCUMENTS

2004/0130785 A1* 7/2004 Yun .......................... G02B 3/08
359/565
2008/0239444 A1 10/2008 Aota et al.
(Continued)

FOREIGN PATENT DOCUMENTS

DE 10 2011 102 355 A1 11/2012
DE 10 2014 207 058 A1 10/2015
(Continued)

OTHER PUBLICATIONS

English translation of PCT International Search Report for PCT/EP2019/081926, mailed Feb. 25, 2020, 4 pages.
(Continued)

*Primary Examiner* — Mahidere S Sahle
(74) *Attorney, Agent, or Firm* — De Witt LLP

(57) ABSTRACT

A device and method of compensating for the temperature dependence of a facet lens used for determining the topography of an eye. According to the invention, temperature sensors are present for determining the temperature of the facet lens. In addition, the temperature dependence of the beam angles of the beam bundles is stored in a control and evaluation unit, which, in addition to the temperature of the facet lens transmitted by the temperature sensors, are taken into account by the control and evaluation unit when evaluating the recordings of the image recording unit. The device and method are described in the context of facet lenses that are used to determine the topography of an eye. However, in principle, they are usable wherever an existing temperature dependence, in particular of optical components, should be compensated for.

20 Claims, 2 Drawing Sheets

(51) Int. Cl.
*G02B 7/00* (2021.01)
*G01B 11/255* (2006.01)

(58) Field of Classification Search
USPC .......................................................... 351/212
See application file for complete search history.

(56) References Cited

U.S. PATENT DOCUMENTS

| | | |
|---|---|---|
| 2012/0026466 A1 | 2/2012 | Zhou et al. |
| 2014/0078468 A1* | 3/2014 | Bublitz .............. G01B 11/2513 351/212 |
| 2014/0182659 A1* | 7/2014 | Davis .................. H01L 31/0543 136/246 |
| 2015/0083193 A1 | 3/2015 | Ueda |

FOREIGN PATENT DOCUMENTS

| | | |
|---|---|---|
| DE | 10 2017 203 010 A1 | 8/2018 |
| KR | 10 2008 0 033 575 A | 4/2008 |
| WO | WO 2014/074572 A1 | 5/2014 |

OTHER PUBLICATIONS

PCT International Search Report for PCT/EP2019/081926, mailed Feb. 25, 2020, 5 pages.
Search Report for DE 10 2018 219 9027 dated Nov. 21, 2018, 10 pages.

\* cited by examiner

ARRANGEMENT AND METHOD FOR COMPENSATING FOR THE TEMPERATURE DEPENDENCE OF A FACET LENS FOR DETERMINING THE TOPOGRAPHY OF AN EYE

RELATED APPLICATIONS

This application is a National Phase entry of PCT Application No. PCT/EP2019/081926 filed Nov. 20, 2019, which application claims the benefit of priority to DE Application No. 10 2018 219 902.7 filed, Nov. 21, 2018, the entire disclosures of which are incorporated herein by reference.

TECHNICAL FIELD

The present invention relates to a solution for compensating for the temperature dependence of a facet lens used for determining the topography of an eye.

BACKGROUND

The term keratometry should be understood to mean the measurement of form and shape of the cornea of the eye. An ophthalmometer (also known as keratometer) is used to ascertain the radii of curvature of the cornea both centrally and in the periphery. A special form of keratometry is topography, in which the central and peripheral radii of curvature of the cornea are measured using specific methods and evaluated mathematically.

A method for measuring the corneal surface shape with the aid of so-called keratometers or keratographs has long been known according to the prior art. In the process, a preferably concentric pattern imaged on the cornea is reflected by the tear film of the cornea and recorded by a camera and evaluated. The reflected pattern detected by the camera is distorted depending on the curvature of the cornea. To obtain a determination of the curvature from these reflection signals, the distortions of the pattern have to be compared to a known shape, which is usually chosen as a sphere with a radius of 7.8 mm.

A example system for determining the topography of the cornea of an eye is described in DE 10 2011 102 355 A1. This type of topography measurement is advantageous in that displacements of the measurement system in relation to the patient's eye are only expressed in the measurement data as defocusing (axial displacement) and as a translation of the entire point pattern in the camera image (lateral displacement).

Since useful information is only carried by the relative spacing of the light dots, the measurement is therefore independent of such a displacement. However, in practice this only applies within certain boundaries, specifically for as long as each light beam strikes the part of the corneal surface for which the required angle relationship as per DE 10 2014 207 058 A1 applies. The spatial element in which this applies to all light dots of the pattern is referred to as the "alignment range" of the topography measurement. Since the latter is finite, the device software should check, for each individual measurement, whether the positioning of the measurement system relative to the patient's eye lies within the alignment range. This check is referred to as an "alignment check".

However, the angles of the beams depend on the temperature of the facet lens. On the one hand, it is advantageous to manufacture the facet lens from plastic but, on the other hand, the influences of temperature are more pronounced in plastic than in glass. In this case, the temperature-dependent change in the angles of the beams emerges from the change in the optical power of the facet lens as a result of a change in the geometry and/or the refractive index of the plastic.

Without temperature compensation, the proposed solution in the case of a manufacture from plastic only works in a temperature range of approximately (20±5°) C. This tolerance range, which is rather tight for actual use, therefore makes the solution impractical.

SUMMARY OF THE INVENTION

Example embodiments of the invention provide a solution for the temperature-independent determination of the topography of an eye on the basis of a facet lens. In this case, the facet lens is easy to manufacture, may be formed of plastic, and can be usable in a temperature range from, for example, 10° C. to 40° C.

The problem of compensating for the temperature dependence of a facet lens for determining the topography of an eye, including an illumination unit, a facet lens, an image recording unit, optical elements for separating illumination beam path and detection beam path, and a control and evaluation unit, is addressed in an example embodiment according to the invention by virtue of temperature sensors additionally being present for determining the temperature of the facet lens, by virtue of the temperature dependence of the emission angles of the beams being stored in the control and evaluation unit, and by virtue of the control and evaluation unit being designed to consider the temperature of the facet lens transferred from the temperature sensors and the stored temperature dependences of the emission angles of the beams when evaluating the recordings of the image recording unit.

Example embodiments of the invention for compensating for the temperature dependence of a plastic lens are provided, in particular, for facet lenses that are used to determine the topography of an eye. However, in principle, the proposed solution is usable wherever an existing temperature dependence, in particular of optical components, should be compensated for.

BRIEF DESCRIPTION OF THE DRAWINGS

The invention is described in more detail below on the basis of example embodiments. In this respect.

DETAILED DESCRIPTION

Example embodiments of the invention are based on the use of a facet lens as described in DE 10 2011 102 355 A1, for example. In this case, the system consists of the facet lens, which is illuminated with planar waves by an illumination unit, an image recording unit, and a control and evaluation unit. In this case, the image recording unit is designed for telecentric, distance-independent image capture. As already mentioned, this type of topography measurement is advantageous in that displacements of the measurement system in relation to the patient's eye are merely expressed in the measurement data as an axial or lateral displacement of the entire point pattern in the camera image. This emerges from the fact that, on account of the measurement principle, the normal vector for each light dot on the corneal surface is geometrically known independently of the specific measurement and, for the purposes of reconstructing the surface, can be assigned to the respective light dot by determining the associated reference point. Depending on the manufacturing tolerances of the measurement system, the normal vectors are assumed to be known or are calibrated accordingly for each individual device.

An example arrangement for compensating for the temperature dependence of a facet lens for determining the topography of an eye includes an illumination unit, a facet lens, an image recording unit, optical elements for separating illumination beam path and detection beam path, and a control and evaluation unit.

According to example embodiment of the invention, temperature sensors are additionally present for the purposes of determining the temperature of the facet lens. Furthermore, the temperature dependences of the emission angles of the beams for the facet lens and hence of the normal vectors at the corneal surface are stored in the control and evaluation unit. In particular, the control and evaluation unit is designed to consider the temperature of the facet lens transferred from the temperature sensors and the stored temperature dependences of the emission angles of the beams when evaluating the recordings of the image recording unit. To this end, the temperature sensors are arranged in the immediate vicinity of, on or in the facet lens and are read following the measurement in addition to the image recording unit and stored where necessary.

Figure 1:
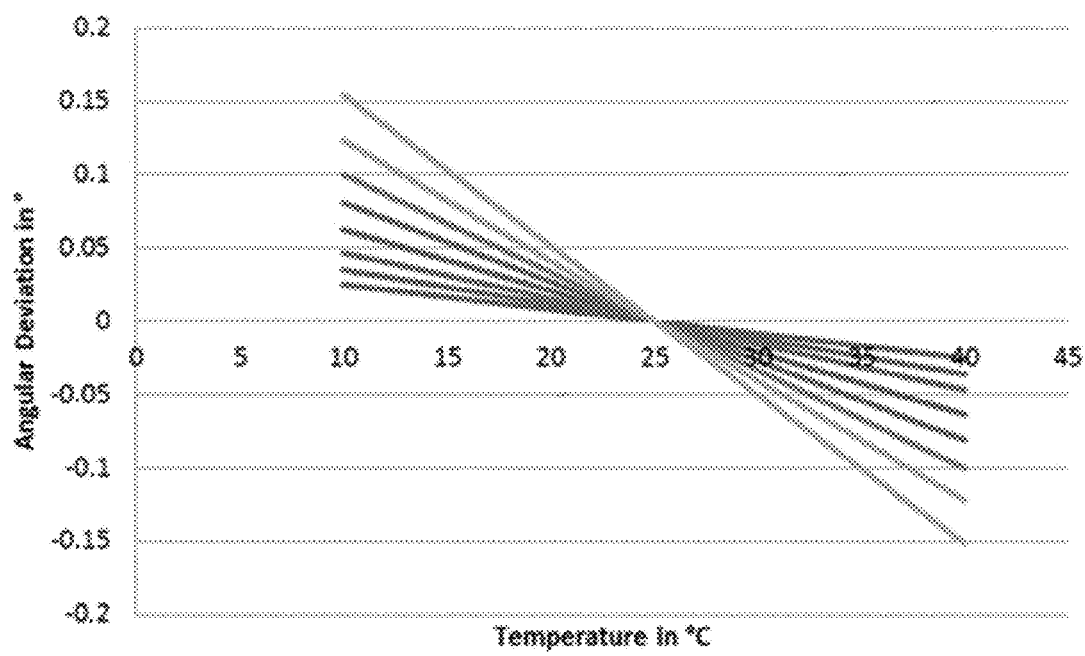
FIG. 1: depicts the dependence of the beam directions on the temperature for 8 rings of a facet lens.

In this respect, FIG. 1 illustrates, in example fashion, the dependence of the beam directions on the temperature for 8 rings of a facet lens. The illustration shows a linear dependence of the deviation of the beam directions. There are no deviations of the emission angles of the beams of the individual rings of the facet lens at a temperature of 25° C.

The temperature dependences of the emission angles of the beams for the facet lens, to be stored in the control and evaluation unit, should be ascertained in advance for a facet lens design.

For as long as the design of the facet lens remains unchanged, it is sufficient to use one sample for determining the temperature dependence.

The determination of the temperature dependence of the emission angles of the beams emerges from an optical simulation and/or a measurement by use of a reference body.

In accordance with a first configuration, a reference specimen is used as a facet lens for the purposes of determining the temperature dependence of the emission angles of the beams, the reference body being a precisely manufactured glass sphere with a known radius.

The angles of the beams can be calculated from the deviations of the recorded point pattern from the expected point pattern. In the process, a temperature range that is as large as possible is covered in order to also take account of an elevated internal temperature in the measurement device.

Figure 4:
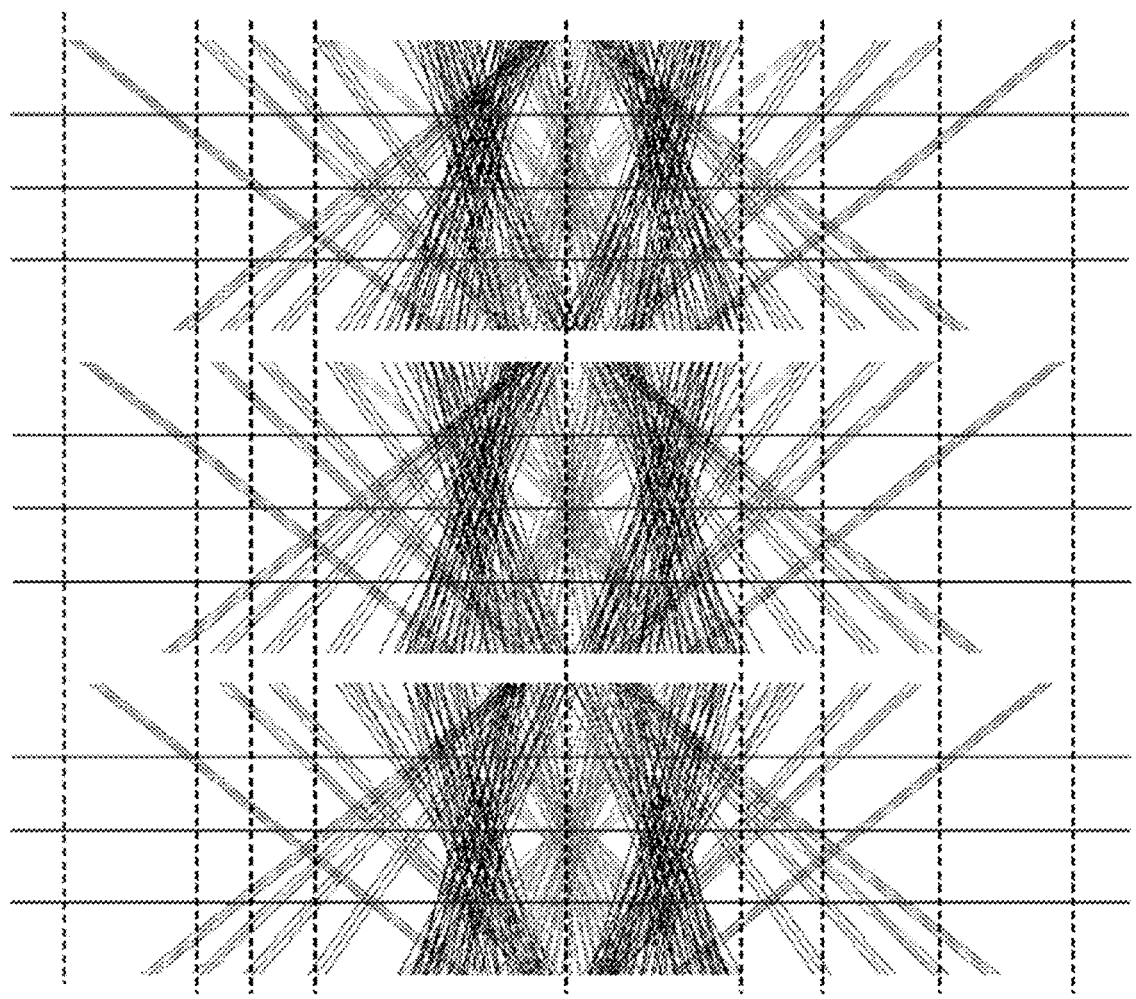
FIG. 4: depicts a comparison of centroid and marginal rays of a plurality of beams for three different temperatures.

To this end, FIG. 4 illustrates a comparison of the centroid and marginal rays of a plurality of beams for three different temperatures. Dashed, vertical auxiliary lines were inserted into the drawing in order to highlight the different emission angles of the beams of the individual rings of the facet lens more clearly. The 3-dimensional intersection of the beams respectively describes the alignment range.

In an example method for compensating for the temperature dependence of a facet lens for determining the topography of an eye, a facet lens is illuminated by an illumination unit and the pattern reflected by the eye is recorded by an image recording unit and transmitted to a control and evaluation unit. The illumination beam path and detection beam path are separated by use of optical elements.

According to the invention, the temperature of the facet lens is additionally determined by application of temperature sensors, the temperature dependence of the emission angles of the beams is stored in the control and evaluation unit, and the control and evaluation unit considers the temperature of the facet lens transferred from the temperature sensors and the stored temperature dependences of the emission angles of the beams when evaluating the recordings of the image recording unit. To this end, the temperature is measured in the direct vicinity of, on or in the facet lens, wherein the temperature is measured before, during and/or after the recording carried out by the image recording unit and transmitted to and stored by the control and evaluation unit.

In respect of the temperature dependence of the emission angles of the beams to be stored in the control and evaluation unit, reference is made to FIG. 1 which illustrates the dependence of the beam directions on the temperature for 8 rings of a facet lens in exemplary fashion. The illustration shows a linear dependence of the deviation of the beam directions. There are no deviations of the emission angles of the beams of the individual rings of the facet lens at a temperature of 25° C.

The determination of the temperature dependence of the emission angles of the beams is implemented in advance for each facet lens by way of an optical simulation and/or by way of a measurement by means of a reference body.

In this case, the temperature dependence can be determined by way of the description using a mathematical function, the mathematical function for example being linear.

A description by way of a linear function is possible since the curve of the refractive index $\Delta n/\Delta T$ of the material used in our facet lens is approximately linear in the utilized temperature range.

Figure 2:
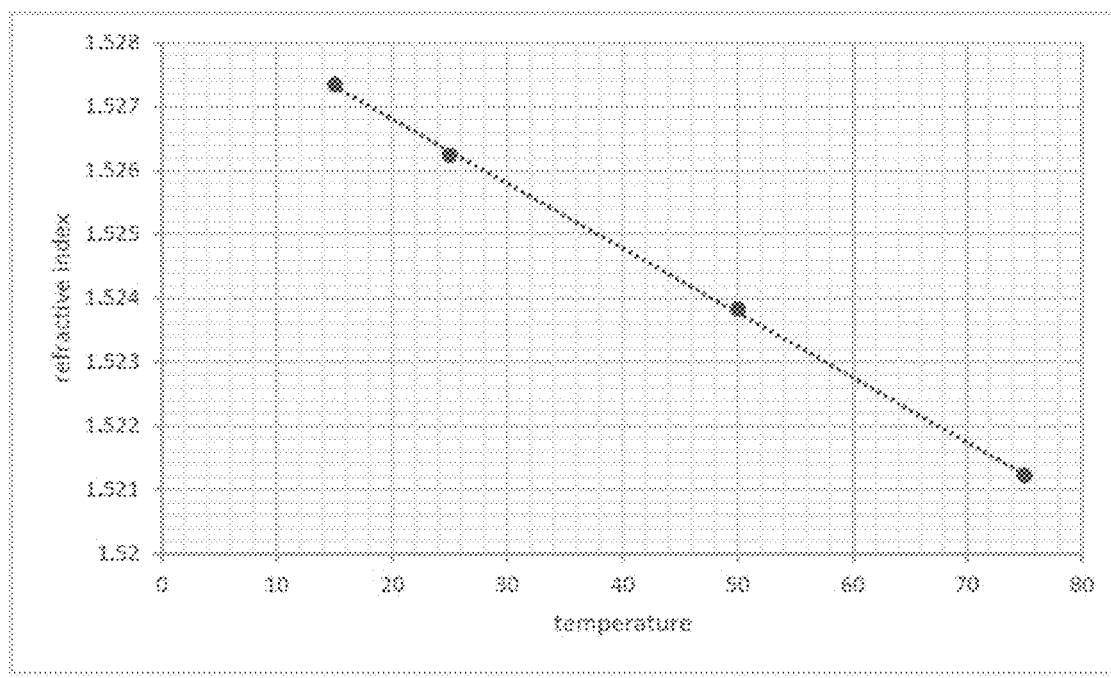
FIG. 2: depicts the dependence of the refractive index n on the temperature T.

To this end, FIG. 2 shows the dependence of the refractive index n on the temperature T, said dependence exhibiting a linear curve.

Under the assumption that the thermal expansion is linear, a linear dependence also arises for the expansion of the lens radius R:

$$R(\Delta T) := R_0 + \alpha_{therm} \cdot R_0 \cdot \Delta T$$

where $R_0$ denotes the radius,
$\alpha_{therm}$ denotes the linear coefficient of expansion, and
$\Delta T$ denotes the temperature change of the facet lens.

On the basis of an estimate with a simple thin lens, the global effect, i.e., the focal length effect, is therefore also linear. The change in the refractive index $\Delta n$ $$n(\Delta T) := \Delta n \cdot \Delta T + n_{25}$$

yields the focal length f of the facet lens as a function of the temperature:

$$f(\Delta T) := \frac{1}{n(\Delta T) - 1} \cdot R(\Delta T)$$

where R. denotes the radius,
n denotes the refractive index, and

ΔT denotes the temperature change of the facet lens.

Figure 3:
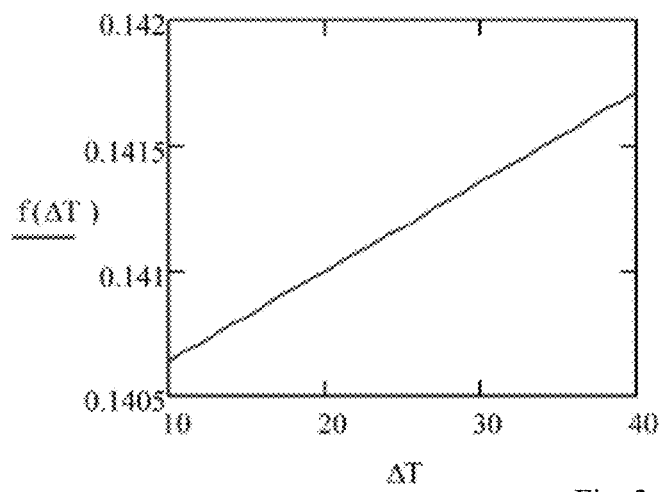
FIG. 3: depicts the dependence of the focal length f on the temperature T.

To this end, FIG. 3 shows the dependence of the focal length f on the temperature T, said dependence likewise exhibiting a linear curve.

Transferred to the angles of the individual facet angles, this means that the effect is always linear. However, the magnitude of this effect is different in this case and depends on the respective chief ray angle.

Local effects, such as the effect on the divergence of the beams that are in fact collimated to the best possible extent (planar wavefront), and hence of the distance independence of the measurement, cannot be calibrated in respect of temperature but are probably substantially smaller and negligible.

The temperature dependence is determined by way of the description using a mathematical function, the mathematical function for example being logarithmic. This alternative option is possible since logarithmic temperature dependences exist in practice.

In accordance with a first configuration of the method, a reference facet lens and, as a reference body, a precisely manufactured glass sphere with a known radius are used for the purposes of determining the temperature dependence of the emission angles of the beams.

The angles of the beams can be calculated from the deviations of the recorded point pattern from the expected point pattern.

In order to also take account of an elevated internal temperature of the measuring device, the temperature dependence is determined for an admissible temperature range from 10° C. to 40° C.

To this end, FIG. 4 illustrates a comparison of the centroid and marginal rays of a plurality of beams for three different temperatures. Dashed, vertical auxiliary lines were inserted into the drawing in order to highlight the different emission angles of the beams of the individual rings of the facet lens more clearly. The 3-dimensional intersection of the beams respectively describes the alignment range. Moreover, this visualizes the temperature dependence better.

A second example configuration of the method relates to the determination of the temperature dependence. Since the facet lens largely has rotational symmetry, the determination can be simplified to the effect of being implemented only once for a facet ring.

However, an increase in the accuracy can be obtained by virtue of the temperature dependence being determined multiple times for each facet ring and the measurement values being averaged.

The third example configuration of the method relates to calibration of each facet lens during the manufacture to a normal temperature of 25° C. Each of the 650 or even more individual facets is calibrated during the calibration with a reference sphere, which is required in any case, the angle of incidence of the respective normal vector being stored for each facet. The function of the temperature compensation is then formulated for this base temperature.

The temperature dependence of the emission angles of the beams at each facet lens determined by the optical simulation and/or by the measurement by means of a reference body is then adapted to each individual facet lens during this calibration.

In the simplest case, the combination by calculation can be linear, where the constant component originates from the calibration of the individual device and the gradient of the straight line originates from the known temperature dependence according to the optical calculation or reference measurement. From this, the normal vectors emerge for the temperature-compensated reconstruction of the topography.

However, it would also be possible to admit further functions. By way of example, logarithmic or exponential functions often lend themselves to this end, as these are often expected in the case of temperature effects.

The temperature-dependent alignment range can be ascertained either as a 3-dimensional intersection of a multiplicity of beams with temperature-dependent angles (see FIG. 4) or by experiment on the reference sphere.

For example, the intersection of the beams is realized using the angle calibration for each individual device. In simplified fashion, it is alternatively possible to ascertain and calculate the difference between the ideal alignment point of the individual device and the ideal alignment point according to the model or reference device.

In accordance with a fourth example configuration of the method, the calibration of every facet lens during the manufacture can be dispensed with if the manufacturing tolerances are tight.

Examples of present invention provide a solution for the temperature-dependent determination of the topography of an eye on the basis of a facet lens, the latter being usable in a broad temperature range from 10° C. to 40° C. despite a simple manufacture from plastic.

It may be expedient to use the measures described here even if the temperature dependence is corrected by hardware measures. This is expedient since each facet can be accurately calibrated on an individual basis by means of software while hardware measures tend to address global effects.

Residual aberrations remain depending on the configuration of the hardware measures and can be compensated for using the solution described here. The combination is moreover advantageous in that the alignment range is reduced less as a result of a change in temperature.

Example embodiments of the invention provides a solution for determining the topography of an eye, in which the compensation of the temperature dependence of a facet lens is realized in a simple and convenient manner.

Although active temperature control of the facet lens would be possible as a matter of principle, it would be more expensive and/or impractical. The same applies to a production of the facet lens from a temperature-stable material. Nor is there any point in using devices with a facet lens without temperature compensation, since these devices could only be used in rigorously temperature-controlled spaces.

The invention claimed is:

1. An arrangement that enables compensating for temperature dependence of a facet lens used to determine topography of an eye, the arrangement comprising:
    an illumination unit;
    the facet lens;
    an image recording unit;
    optical elements that separate an illumination beam path and a detection beam path;
    a control and evaluation unit; and
    temperature sensors that are additionally present that determine a temperature of the facet lens;
    wherein temperature dependence of emission angles of beams is stored in the control and evaluation unit; and
    wherein the control and evaluation unit is configured to consider the temperature of the facet lens transferred from the temperature sensors and to utilize the stored temperature dependences of the emission angles of the beams when evaluating recordings of the image recording unit to compensate for the temperature dependence of the facet lens.

2. The arrangement as claimed in claim 1, wherein the temperature sensors are arranged in an immediate vicinity of, on or in the facet lens.

3. The arrangement as claimed in claim 1, wherein the determination of the temperature dependence of the emission angles of the beams emerges from an optical simulation and/or a measurement by use of a reference body.

4. The arrangement as claimed in claim 1, wherein a reference specimen is used in place of the facet lens for the determination of the temperature dependence of the emission angles of the beams.

5. The arrangement as claimed in claim 4, wherein the reference specimen comprises a precisely manufactured glass sphere with a known radius.

6. A method that enables compensating for temperature dependence of a facet lens used to determine topography of an eye, wherein the facet lens is illuminated by an illumination unit, a pattern reflected by the eye is recorded by an image recording unit and transmitted to a control and evaluation unit, an illumination beam path and a detection beam path being separated by use of optical elements, the method comprising:
   determining the temperature of the facet lens is by use of temperature sensors;
   storing temperature dependence of emission angles of beams in the control and evaluation unit; and
   considering, by application of the control and evaluation unit, the temperature of the facet lens transferred from the temperature sensors and utilizing the stored temperature dependences of the emission angles of the beams when evaluating the recordings of the image recording unit to compensate for the temperature dependence of the facet lens.

7. The method as claimed in claim 6, further comprising measuring the temperature in an immediate vicinity of, on or in the facet lens.

8. The method as claimed in claim 6, further comprising measuring the temperature before, during, after or a combination of the foregoing of recording carried out by the image recording unit and transmitting the temperature to the control and evaluation unit and storing the temperature by the control and evaluation unit.

9. The method as claimed in claim 6, further comprising implementing the determination of the temperature dependence of the emission angles of the beams by way of an optical simulation and/or by way of a measurement using a reference body.

10. The method as claimed in claim 9, further comprising determining the temperature dependence by way of a description using a mathematical function.

11. The method as claimed in claim 10, wherein the mathematical function is linear.

12. The method as claimed in claim 10, wherein the mathematical function is logarithmic.

13. The method as claimed in claim 9, further comprising using a precisely manufactured glass sphere with a known radius as the reference body.

14. The method as claimed in claim 6, further comprising using a reference specimen as the facet lens for the determination of the temperature dependence of the emission angles of the beams.

15. The method as claimed in claim 6, further comprising determining the temperature dependence for an admissible temperature range from 10° C. to 40° C.

16. The method as claimed in claim 6, further comprising determining the temperature dependence of a facet ring once.

17. The method as claimed in claim 6, further comprising determining the temperature dependence of a facet ring multiple times and averaging measurement values.

18. The method as claimed in claim 6, further comprising calibrating each facet lens during manufacture to a normal temperature of 25° C.

19. The method as claimed in claim 6, further comprising determining the temperature dependence of the emission angles of the beams by an optical simulation, or by measurement by use of a reference body adapted to each facet lens which was calibrated during manufacture to a normal temperature of 25° C. or by a combination of the foregoing.

20. The method as claimed in claim 6, further comprising dispensing with calibration of every facet lens during the manufacture if manufacturing tolerances are tight.

* * * * *